United States Patent
Stothers et al.

(10) Patent No.: US 10,018,580 B2
(45) Date of Patent: Jul. 10, 2018

(54) APPARATUS AND METHOD FOR DETECTING WATER OR ICE

(71) Applicant: Ultra Electronics Limited, Greenford, Middlesex (GB)

(72) Inventors: Ian McGregor Stothers, Saham Toney (GB); Robert William Saunders, London (GB)

(73) Assignee: Ultra Electronics Limited, Greenford (GB)

( * ) Notice: Subject to any disclaimer, the term of this patent is extended or adjusted under 35 U.S.C. 154(b) by 278 days.

(21) Appl. No.: 14/760,079

(22) PCT Filed: Jan. 10, 2014

(86) PCT No.: PCT/GB2014/050069
§ 371 (c)(1),
(2) Date: Jul. 9, 2015

(87) PCT Pub. No.: WO2014/108695
PCT Pub. Date: Jul. 17, 2014

(65) Prior Publication Data
US 2015/0346122 A1 Dec. 3, 2015

(30) Foreign Application Priority Data
Jan. 11, 2013 (GB) .................................. 1300468.4

(51) Int. Cl.
*G01K 1/00* (2006.01)
*G01N 25/72* (2006.01)
(Continued)

(52) U.S. Cl.
CPC ............. *G01N 25/72* (2013.01); *B64D 15/14* (2013.01); *B64D 15/20* (2013.01); *B64D 43/00* (2013.01)

(58) Field of Classification Search
CPC .................................. G01N 25/72; B64D 43/00
(Continued)

(56) References Cited

U.S. PATENT DOCUMENTS 6,328,467 B1 12/2001 Keyhani
7,580,777 B2 8/2009 Smith et al.
(Continued)

FOREIGN PATENT DOCUMENTS

GB 2483530 A 3/2012
WO WO 2008/145985 A2 12/2008

*Primary Examiner* — Anthony Ho
(74) *Attorney, Agent, or Firm* — Blank Rome LLP

(57) ABSTRACT

The present invention relates to an apparatus and method for detecting the presence of water or ice on a structure, for example on the surface of an aircraft. One or more separate heaters are thermally coupled to a structure (for example on the back of wing leading edge skins). A controller applies power to the heaters to heat the different regions of the surface of the structure. The controller detects the presence of water or ice by comparing the power required to achieve the desired surface temperature, and a reference power, where the reference power is the power required to heat the surface of the structure to the same temperature if the structure were in a dry air environment (i.e. an environment devoid of water). If the power consumed by the heater is greater than the reference power, the presence of water or ice is inferred.

48 Claims, 8 Drawing Sheets

Slave Temperature Control Scheme

(51) Int. Cl.
*B64D 43/00* (2006.01)
*B64D 15/14* (2006.01)
*B64D 15/20* (2006.01)

(58) Field of Classification Search
USPC ........................................................ 702/130
See application file for complete search history.

(56) References Cited

U.S. PATENT DOCUMENTS

| 9,676,485 B2* | 6/2017 | Stothers | B64D 15/20 |
| 2009/0149997 A1 | 6/2009 | Stothers | |
| 2009/0230239 A1 | 9/2009 | Stothers | |
| 2010/0243811 A1 | 9/2010 | Stothers | |
| 2012/0061482 A1* | 3/2012 | Stothers | H05B 1/0236 |
| | | | 237/2 R |

* cited by examiner

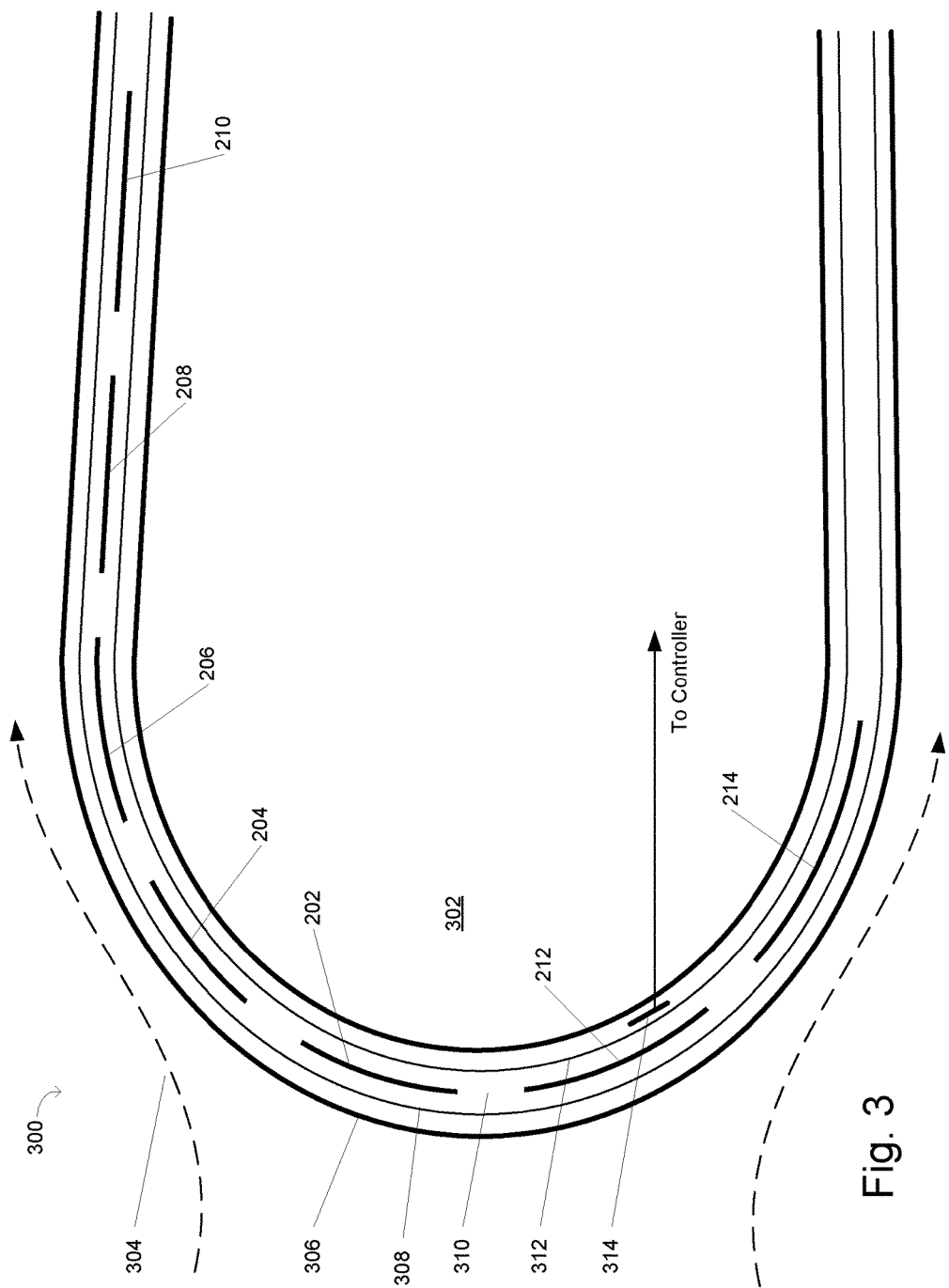

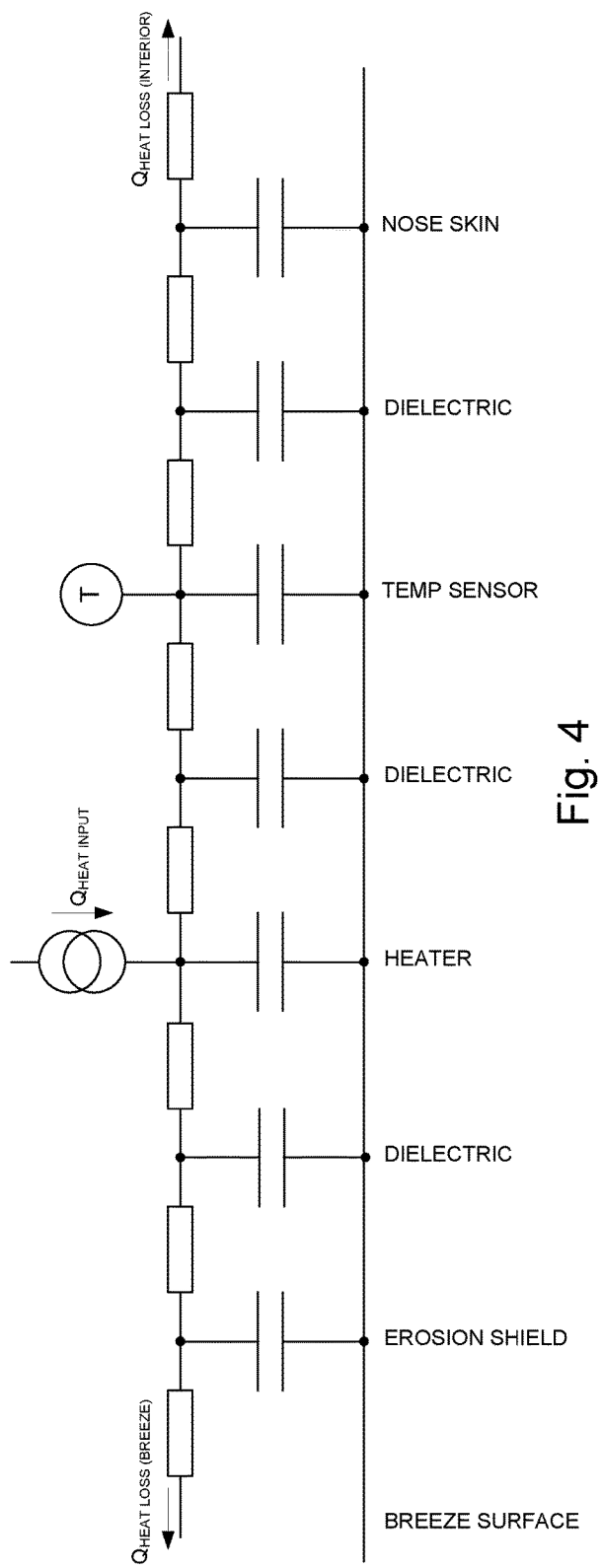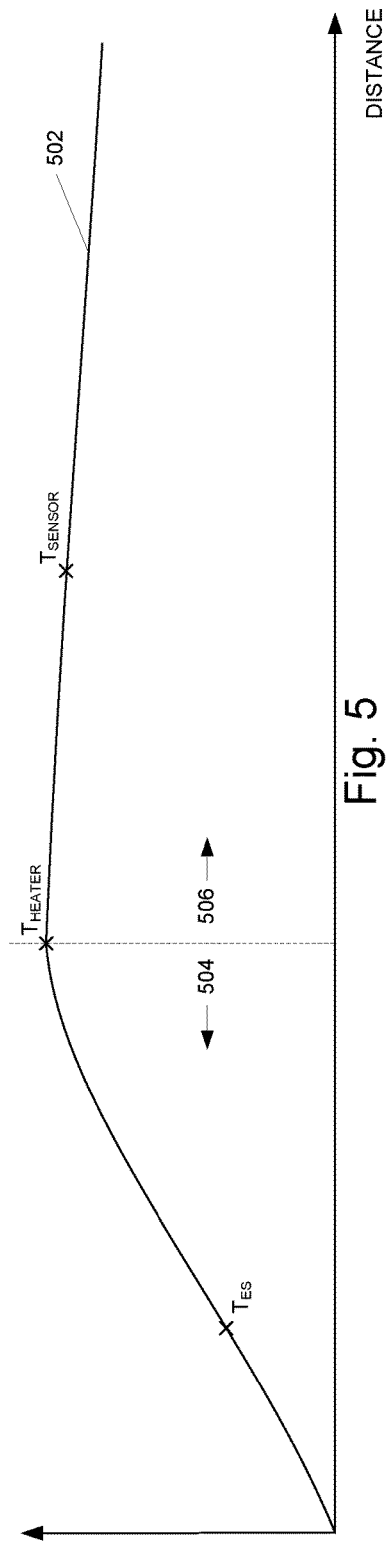

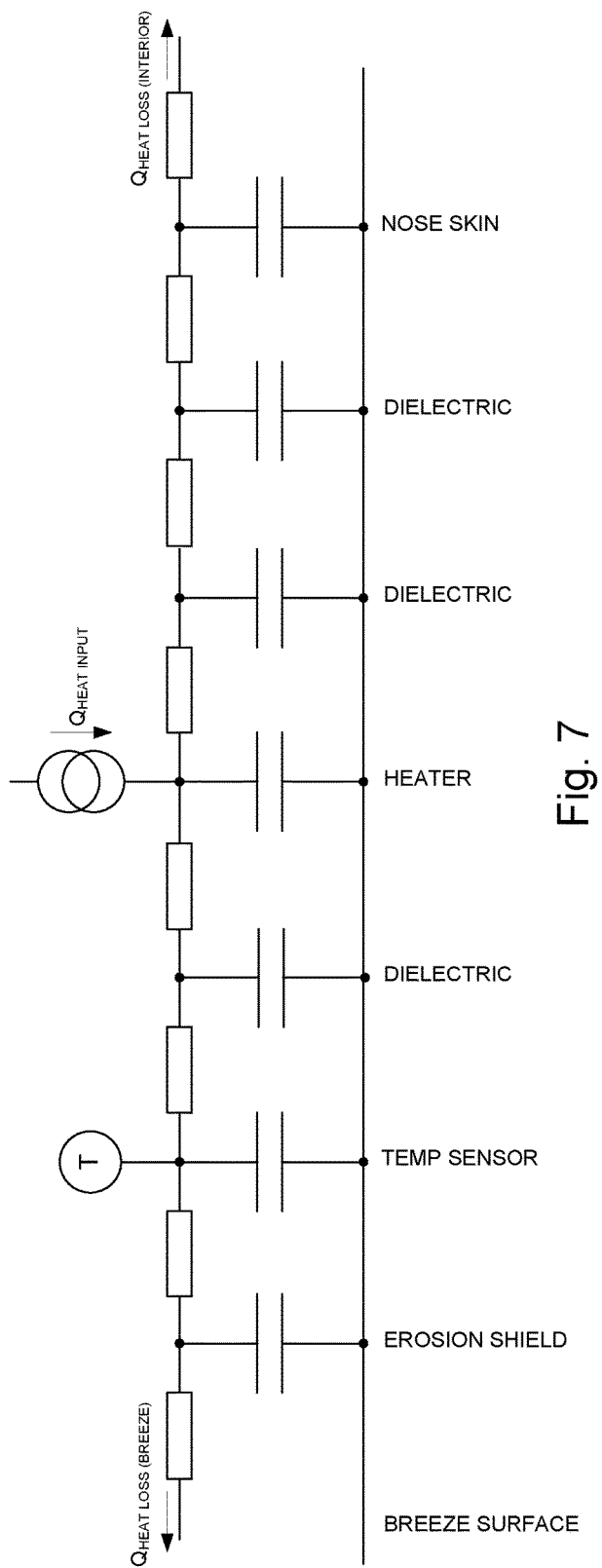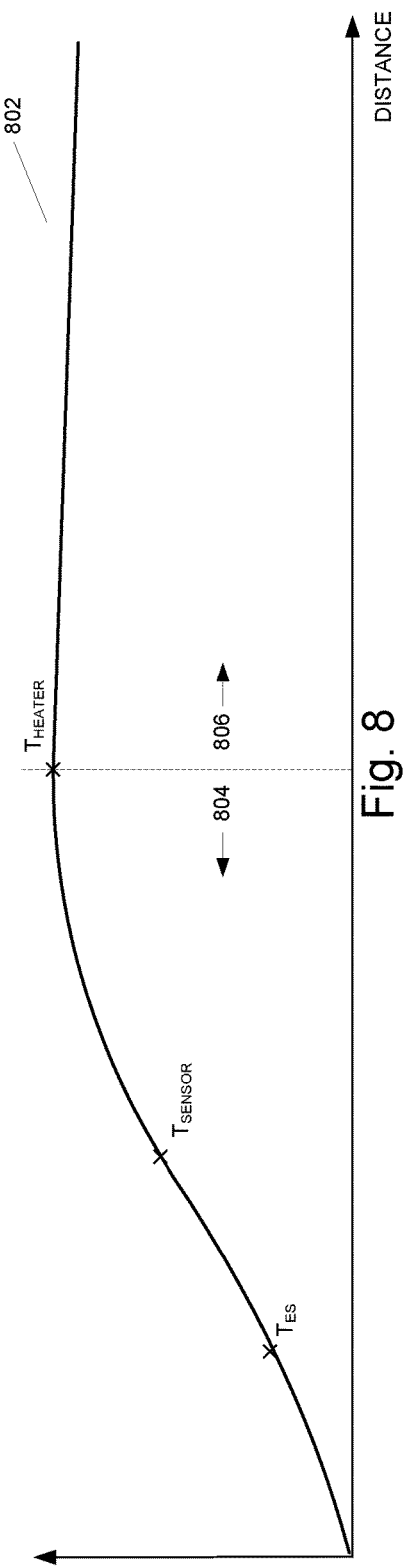
Fig. 7
Fig. 8

Slave Temperature
Control Scheme

APPARATUS AND METHOD FOR DETECTING WATER OR ICE

FIELD OF THE INVENTION

The present invention relates to an apparatus and method for detecting the presence of water or ice on a structure, for example on the surface of an aircraft.

BACKGROUND OF THE INVENTION

Devices for detecting the presence of water or ice on structures, for example aircraft structures, are known. Example devices include those that detect ice formation using optical means (i.e. detecting a change in opacity or refractive index around a sensor). Others include those that monitor changes in a resonant frequency of a structure (i.e. the accumulation of ice on a structure alters its resonant frequency).

Preferably, ice detection methods only detect the impingement of water that is likely to 'stick' to the surface of a structure. Water crystals, for example, usually bounce off a structure, and thus are less likely to accrete on a surface and thus are unlikely to cause problems.

Some devices used to detect the presence of water or ice on a structure include Pitot-type detectors, which ingest all forms of water, including crystals (which usually just bounce off the structure). They cannot distinguish between 'sticky' and 'non-sticky' water. Pitot-type detectors can also become blocked (and need regular cleaning).

In GB 2483530, we described a scheme in which the ice detection system was driven to detect an icing condition based on the power required to heat first and second heaters to different temperatures in a temperature range. However, it has been found that the described schemes sometimes do not detect icing conditions due to heat spread through the skin and due to insufficient temperature measurement accuracies.

There are also developments in the FAA regulations on Supercooled Large Droplets (forming Appendix O of Part 25), which will require systems to detect their presence. Many of the above-mentioned methods are not appropriate for detecting such droplets.

We have therefore appreciated the disadvantages of known devices for detecting the presence of water or ice on the surface of a structure (including SLDs), and the need for an improved method and device.

SUMMARY OF THE INVENTION

The present invention therefore provides a method of detecting the presence of water or ice on a surface of a structure, the structure being exposable to an impinging airflow, the method comprising the steps of: supplying a first heater with a first power, the first heater being in thermal contact with a first region of a structure exposable to an impinging airflow, the first power being sufficient to heat a surface of the structure at the first region; supplying each of one or more second heaters with a respective power, each of the one or more second heaters being in thermal contact with a respective region of the structure exposable to an impinging airflow, each of the respective powers being sufficient to heat a surface of the structure at the respective region; and detecting the presence of water or ice on the surface of a structure at a respective region by comparing a power consumed by a respective heater to achieve a temperature at the surface of the structure at the respective region with a reference power for the respective heater, wherein the reference power is a power for applying to the respective heater to achieve the same temperature at the surface of the structure at the respective region if the respective region of the structure was subjected to an environmental condition that was substantially devoid of water, and wherein water or ice is detected when the power consumed by the respective heater is greater than the reference power.

By comparing a power required to power a heater to achieve a surface temperature to the power required to power the heater to achieve the same temperature if the region being heated were subjected to an environmental condition devoid of water, this enables a determination of whether or not water or ice is present in that particular region. As such, used on an aircraft wing, for example, enables a determination of whether or not there is water or ice accumulating on the surface of a wing, which can be relayed back to the pilot, or used in the control of a de-icing system.

By using multiple regions (first and one or more second regions), a picture of regions having ice or water detected therein may be mapped, to enable an impingement profile to be built up. From knowledge of the placement of the regions, a determination of how far back water or ice is impinging on the surface, which can be used to determine the type or size of water or ice droplets that are impinging the surface.

The surface temperature may be calculated by: measuring a temperature of the heater; and calculating the surface temperature from the temperature of the heater, the power applied to the heater, and at least one thermal resistance between the heater and the surface of the structure.

The method may also comprise: measuring a temperature of the first heater; and controlling the first power applied to the first heater using the measured temperature of the heater. Preferably, the first power applied to the heater is controlled such that the surface temperature is sufficient to cause evaporation of water or ice in contact with the surface of the structure at the first region.

The method may also comprise: controlling the respective power applied to each of the second heaters such that the surface temperature at the respective region is substantially the same as the surface temperature of the first region. Advantageously, this control scheme aims to achieve a uniform temperature over the entire outer surface of the structure. Maintaining a uniform temperature across the structure enables errors in the power difference calculations to be reduced. The thermal conductivity of the surface may be high and if there are temperature variations from the surface of one heated region to another then there is significant heat leakage between regions, which result in large errors in power difference calculations.

In embodiments, the first region of a structure may be located on a leading edge of the structure, and wherein one of the respective regions thermally coupled to one of the second heaters may be adjacent and aft of the first region in a direction of an impinging airflow on the structure. In these embodiments, a further region in thermal contact with another of a respective one of the second heaters is adjacent and aft of the one of the respective regions in a direction of an impinging airflow on the structure.

The method may also comprise: identifying a region aft of the first region having water or ice detected thereon; and generating a signal if a distance of the identified region aft of the first region is greater than a threshold distance. This enables a determination of the size of water or ice droplets impinging on the surface of the structure; larger droplets will impinge further back (from the first region) than smaller droplets.

In embodiments, the first surface temperature is controlled to be greater than or equal to 50° C. above a temperature of the environment to which the structure is exposed. This ensures that there is sufficient margin over the surrounding environment.

The method may also comprise calculating the reference power. This may be performed by: determining a temperature drop at the surface of the structure; determining a mass of air flowing past a region of the structure with which the heater is in thermal contact; calculating the reference power depending on the temperature drop at the surface of the structure and the mass of air flowing past the region of the structure.

Determining a temperature drop at the surface of the structure may comprise: calculating a surface temperature of the surface at a region; measuring a total temperature of the environment surrounding the structure; and subtracting the total temperature of the environment surrounding the structure from the surface temperature.

Determining a mass of air flowing past a region of the structure may comprise: measuring an airspeed of the structure; calculating a density of the air flowing past the structure using a measurement of the altitude of the structure, or air pressure, and a calculation of the static air temperature; and calculating the mass of air flowing past a region of the structure using the airspeed and density.

The reference power may be calculated using the relationship:

$$P = K(T_{surface} - TAT)V\rho$$

where:
K is the heat transfer coefficient of the surface to the air
$T_{surface}$ is a surface temperature at a region
TAT is the total air temperature of the environment surrounding the structure
V is the free-stream air speed
$\rho$ is the density of the air surrounding the structure.

The density of the air surrounding the structure may be determined by the relationship:

$$\rho = \rho_0 T_0 \frac{e^{(-altitude/ref\_alt)}}{SAT}$$

Where:
$\rho_0$ is the air density at standard Temperature and Pressure
$T_0$ is the standard Temperature
altitude is the altitude of the structure (in ft)
ref_alt is a reference altitude (in ft)
SAT is the Static Air Temperature.

The density of the air surrounding the structure may be determined by the relationship:

$$\rho = \rho_0 \frac{PT_0}{P_0 SAT}$$

where:
$\rho_0$ is the air density at standard Temperature and Pressure
$T_0$ is standard Temperature
P is the Static Air Pressure
$P_0$ is the Standard Air Pressure
SAT is the Static Air Temperature.

A method of detecting an icing condition in which ice may form on a structure exposable to an impinging airflow is also proposed. The method may comprise: detecting the presence of water on the surface of a structure exposable to an impinging airflow according to the method described above; detecting an air temperature of the environment external to the structure; detecting an icing condition dependent on the detection of the presence of water on the surface of the structure and the air temperature being substantially at or below 10° C. The method may also comprise generating a signal if an icing condition is detected.

The present invention also provides apparatus for detecting the presence of water or ice on a surface of a structure, the structure being exposable to an impinging airflow, the apparatus comprising: a first heater thermally coupleable to a first region of structure exposable to an impinging airflow, a first temperature sensor thermally coupled to the first heater for sensing the temperature of the first heater and for outputting a first temperature signal; one or more second heaters thermally coupleable to a respective region of the structure, for each of the one or more second heaters, a respective temperature sensor thermally coupled thereto for sensing the temperature of the respective second heater and for outputting a respective temperature signal; a controller coupled to the first heater, first temperature sensor, each of the one or more second heaters and each of the respective temperature sensors and for controllably applying power to the first heater and one or more second heaters, the controller being configured to: supply the first heater with a first power, the first power being sufficient to heat a surface of the structure at the first region; supply each of the one or more second heaters with a respective power, the respective power being sufficient to heat a surface of the structure at the respective region; and detect the presence of water or ice on the surface of a structure at a respective region by comparing the power consumed by a respective heater to achieve a temperature at the surface of the structure at the respective region with a reference power for the respective heater, wherein the reference power is a power for applying to the respective heater to achieve the same temperature at the surface of the structure at the respective region if the respective region of the structure was subjected to an environmental condition that was substantially devoid of water, and wherein the controller detects the presence of water or ice when the power consumed by the respective heater is greater than the reference power.

By comparing a power required to power a heater to achieve a surface temperature to the power required to power the heater to achieve the same temperature if the region being heated were subjected to an environmental condition devoid of water, this enables a determination of whether or not water or ice is present in that particular region. As such, used on an aircraft wing, for example, enables a determination of whether or not there is water or ice accumulating on the surface of a wing, which can be relayed back to the pilot, or used in the control of a de-icing system.

By using multiple regions (first and one or more second regions), a picture of regions having ice or water detected therein may be mapped, to enable an impingement profile to be built up. From knowledge of the placement of the regions, a determination of how far back water or ice is impinging on the surface, which can be used to determine the type or size of water or ice droplets that are impinging the surface.

The controller may be configured to calculate the surface temperature by: receiving the temperature signal; and calculating the surface temperature from the temperature signal, the power applied to the heater, and at least one thermal resistance between the heater and the surface of the structure.

The controller may also be configured to control the first power applied to the first heater using the first temperature signal. Preferably, the first power applied to the heater is sufficient to cause evaporation of water or ice in contact with the surface of the structure at the first region.

The first region of a structure may be located on a leading edge of the structure, and wherein one of the respective regions thermally coupled to one of the second heaters is adjacent and aft of the first region in a direction of an impinging airflow on the structure. A further region in thermal contact with another of a respective one of the second heaters may be adjacent and aft of the one of the respective regions in a direction of an impinging airflow on the structure.

The controller may be configured to control the power applied to each of the one or more second heaters such that the respective surface temperature is substantially the same as the surface temperature of the first region. Advantageously, this control scheme aims to achieve a uniform temperature over the entire outer surface of the structure. Maintaining a uniform temperature across the structure enables errors in the power difference calculations to be reduced. The thermal conductivity of the surface may be high and if there are temperature variations from the surface of one heated region to another then there is significant heat leakage between regions, which result in large errors in power difference calculations.

The first surface temperature may be controlled to be greater than or equal to 50° C. above a temperature of the environment to which the structure is exposed.

In one embodiment, the heater is disposed in a layer between the temperature sensor and a surface of the structure. In alternative embodiments, the temperature sensor is disposed in a layer between the heater and a surface of the structure.

The controller may be configured to calculate the reference power by: determining a temperature drop at the surface of the structure; determining a mass of air flowing past a region of the structure with which the heater is in thermal contact; calculating the reference power depending on the temperature drop at the surface of the structure and the mass of air flowing past the region of the structure.

The controller may be configured to determine a temperature drop at the surface of the structure by: calculating a surface temperature of the surface at a region; measuring a total temperature of the environment surrounding the structure; and subtracting the total temperature of the environment surrounding the structure from the surface temperature.

The controller may also be configured to determine a mass of air flowing past a region of the structure by: measuring an airspeed of the structure; calculating a density of the air flowing past the structure using a measurement of the altitude of the structure, or air pressure, and a calculation of the static air temperature; and calculating the mass of air flowing past a region of the structure using the airspeed and density.

The controller may calculate the reference power using the relationship:

$$P = K(T_{surface} - TAT)V\rho$$

where:
K is the heat transfer coefficient of the surface to the air
$T_{surface}$ is a surface temperature at a region
TAT is the total air temperature of the environment surrounding the structure
V is the free-stream airspeed
$\rho$ is the density of the air surrounding the structure.

The present invention also provides a controller for detecting the presence of water or ice on a surface of a structure, the structure being exposable to an impinging airflow, the controller comprising: an output adapted to supply power to a first heater, the first heater being thermally coupleable to a first region of structure exposable to an impinging airflow, an input adapted to receive a first temperature sensor signal from a first temperature sensor thermally coupleable to the first heater for sensing the temperature of the first heater; one or more second outputs adapted to supply power to respective one or more second heaters, the one or more second heaters being thermally coupleable to a respective region of the structure; one or more second inputs adapted to receive respective temperature sensor signals from respective one or more second temperature sensors, each of the one or more second temperature sensors being thermally coupleable to a respective second heater, and each of the one or more second temperature sensors for sensing the temperature of the respective heaters; the controller being configured to: supply a first power to a first heater, the first power being sufficient to heat a surface of the structure at the first region; supply each of the one or more second heaters with a respective power, the respective power being sufficient to heat a surface of the structure at the respective region; and detect the presence of water or ice on the surface of a structure at a respective region by comparing the power consumed by a respective heater to achieve a temperature at the surface of the structure at the respective region with a reference power for the respective heater, wherein the reference power is a power for applying to the respective heater to achieve the same temperature at the surface of the structure at the respective region if the respective region of the structure was subjected to an environmental condition that was substantially devoid of water, and wherein the controller detects the presence of water or ice when the power consumed by the respective heater is greater than the reference power.

By comparing a power required to power a heater to achieve a surface temperature to the power required to power the heater to achieve the same temperature if the region being heated were subjected to an environmental condition devoid of water, this enables a determination of whether or not water or ice is present in that particular region. As such, used on an aircraft wing, for example, enables a determination of whether or not there is water or ice accumulating on the surface of a wing, which can be relayed back to the pilot, or used in the control of a de-icing system.

By using multiple regions (first and one or more second regions), a picture of regions having ice or water detected therein may be mapped, to enable an impingement profile to be built up. From knowledge of the placement of the regions, a determination of how far back water or ice is impinging on the surface, which can be used to determine the type or size of water or ice droplets that are impinging the surface.

The present invention also provides apparatus for detecting the presence of water or ice on a surface of a structure, the structure being exposable to an impinging airflow, the apparatus comprising: a first heater thermally coupleable to a first region of structure exposable to an impinging airflow, a first temperature sensor thermally coupled to the first heater for sensing the temperature of the first heater and for outputting a first temperature signal; one or more second heaters thermally coupleable to a respective region of the structure, for each of the one or more second heaters, a respective temperature sensor thermally coupled thereto for sensing the temperature of the respective second heater and for outputting a respective temperature signal; a controller coupled to the first heater, first temperature sensor, each of the one or more second heaters and each of the respective temperature sensors and for controllably applying power to the first heater and one or more second heaters, the controller being configured to: supply the first heater with a first power, the first power being sufficient to heat a surface of the structure at the first region; supply each of the one or more second heaters with a respective power, the respective power being sufficient to heat a surface of the structure at the respective region; control the power applied to each of the one or more second heaters such that the respective surface temperature is substantially the same as the surface temperature of the first region; and detect the presence of water or ice on the surface of a structure at a respective region by comparing a power consumed by the respective heater to achieve a temperature at the surface of the surface at the respective region with the a reference power for the respective heater, wherein the reference power is a power for applying to the respective heater to achieve the same temperature at the surface of the structure at the respective region if the respective region of the structure was subjected to an environmental condition that was substantially devoid of water, and wherein the controller detects the presence of water or ice when the power consumed by the respective heater is greater than the reference power.

By comparing a power required to power a heater to achieve a surface temperature to the power required to power the heater to achieve the same temperature if the region being heated were subjected to an environmental condition devoid of water, this enables a determination of whether or not water or ice is present in that particular region. As such, used on an aircraft wing, for example, enables a determination of whether or not there is water or ice accumulating on the surface of a wing, which can be relayed back to the pilot, or used in the control of a de-icing system.

By using multiple regions (first and one or more second regions), a picture of regions having ice or water detected therein may be mapped, to enable an impingement profile to be built up. From knowledge of the placement of the regions, a determination of how far back water or ice is impinging on the surface, which can be used to determine the type or size of water or ice droplets that are impinging the surface.

Furthermore, by using a control scheme wherein the surface temperature of the second regions are controlled to be the same as the surface temperature of the first region, this advantageously aims to achieve a uniform temperature over the entire outer surface of the structure. Maintaining a uniform temperature across the structure enables errors in the power difference calculations to be reduced. The thermal conductivity of the surface may be high and if there are temperature variations from the surface of one heated region to another then there is significant heat leakage between regions, which result in large errors in power difference calculations.

LIST OF FIGURES

The invention will now be described, by way of example only with reference to the accompanying figures, in which:

FIG. 3 is a cross-section of the structure of an aircraft wing section;

FIG. 4 is an illustration of thermal resistances and thermal capacitances of the wing section of FIG. 3;

FIG. 5 is a graph illustrating the variation of temperature over distance within the wing section of FIG. 3;

FIG. 7 is an illustration of thermal resistances and thermal capacitances of the wing section of FIG. 6;

FIG. 8 is a graph illustrating the variation of temperature over distance within the wing section of FIG. 6;

DETAILED DESCRIPTION OF THE PREFERRED EMBODIMENTS

Figure 1:
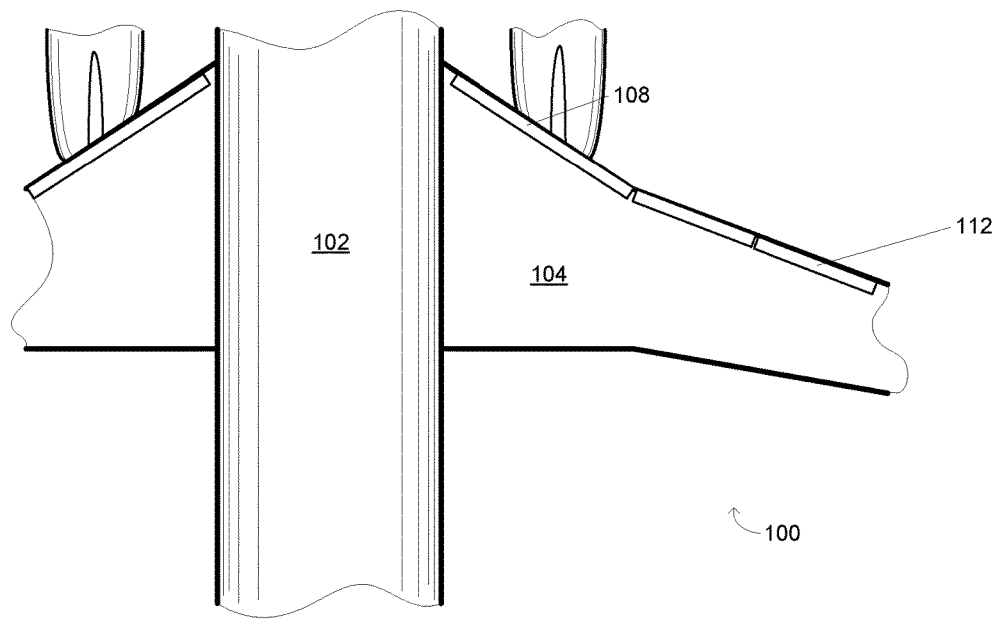
FIG. 1 is an illustration of a portion of an aircraft.

In brief, the present invention uses one or more separate heaters thermally coupled to a structure (for example on the back of wing leading edge skins). A controller applies power to the heaters to heat the different regions of the surface of the structure. The controller calculates a power difference between the power required to achieve the desired surface temperature, and the power required to heat the surface of the structure to the same temperature if the structure were in a dry air environment (i.e. an environment devoid of water). If the power required to heat the surface of the structure to the desired temperature is greater than the power required to heat the surface of the structure to the desired temperature if the structure were in an dry environment, the presence of water or ice is inferred.

We shall first discuss ice protection systems in general. Ice protection systems protect against the build-up of ice on structures. One common application of ice protection systems is on aircraft. During flight, the surfaces of an aircraft can be exposed to water at low temperatures and, if no preventative action is taken, ice can quickly form on the wings, on control surfaces, and on other parts of the aircraft in such a way as to alter the aerodynamic performance of the aircraft (for example by altering the airflow around the aircraft and by adding additional weight to it) with potentially catastrophic consequences. Example ice protection systems are discussed in the following patents and applications in the name of Ultra Electronics Limited® (the content of which are hereby incorporated in their entirety by reference): U.S. Pat. No. 7,580,777, WO2008/145985, US20090149997, US20090230239 and US2010/0243811.

Electrothermal ice protection systems comprise a number of heater devices (such as heater mats), which can be used as anti-icing zones in which a sufficient temperature is maintained at the surface of the wing in order to prevent the formation of ice on and behind the protected zone. These heater devices can also be used as de-icing zones to shed ice that has been allowed to accrete on the protected region. The de-icing mats are cyclically energised in order to melt the interface between the wing and the accreted ice, causing the ice to be shed.

In such an ice protection system it is important to avoid overheating of the heater devices (heating mats) in order to avoid a failure either of the devices or in the structure to which the devices are attached. Many modern aircraft (and other structures) use composite materials, which can suffer damage (delamination of the material, for example) at a relatively low temperature. Temperature 'overshoot' of the heater devices must therefore be controlled whilst maintaining rapid heating of the protected surface(s).

Aircraft are normally subject to a range of different icing conditions during flight, such as different air temperatures, air velocities, relative humidity, and so on, which can depend for example on the location, altitude, orientation, air speed or pitch of the aircraft, the prevailing meteorological conditions, and so on. Different icing conditions can determine not only the temperatures and velocities (and so on) at which ice will form on different parts of the aircraft structure, but also the heat loss from the aircraft structure.

FIG. 1 is an illustration of a portion of an aircraft, showing the placement of heater mats of an ice protection system of an aircraft. The aircraft 100 includes a fuselage portion 102 and a wing portion 104. On the leading edge 106 of the wing 104 are provided a plurality of heating mats.

Each heater mat is divided into a number of heater zones. The number and size of the heater zones are chosen to suit a particular safety model, for example such that up to two heater zones can fail without causing a hazardous or catastrophic failure of the aircraft. In one aircraft design, safety requirements require each heater mat to be divided into six separate heater zones.

However, ice protection systems are known for being power-hungry systems, which can be a burden to the power generation and distribution systems in aircraft. It is sometimes therefore desirable only to use the ice protection systems as and when needed, rather than all the time. There thus remains a need to detect when water or ice is impinging on, or sticking to, the surface of a structure. Once the presence of water and/or ice has been detected, the ice protection systems can be activated.

Figure 2:
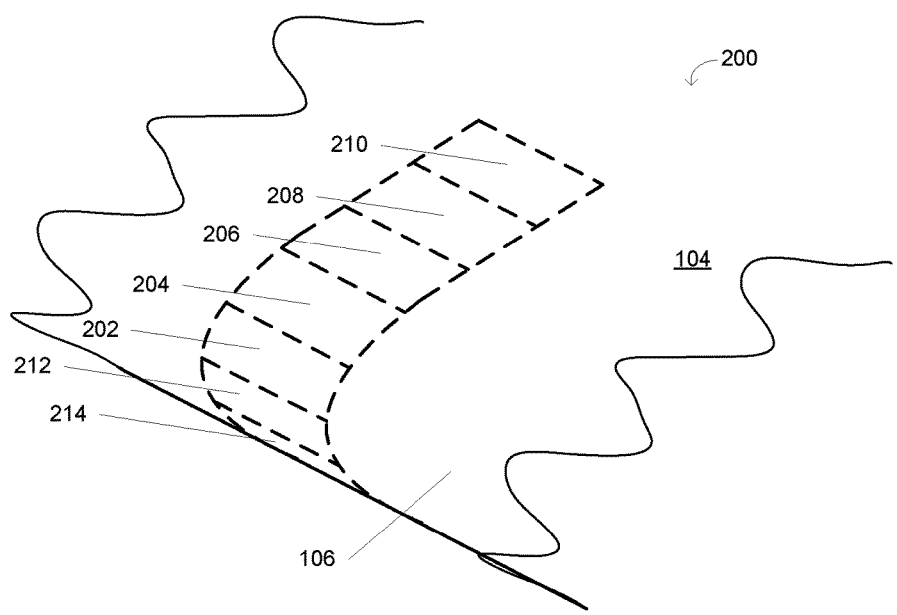
FIG. 2 is an illustration of a portion of the leading edge of an aircraft wing comprising a plurality of heated regions.

FIG. 2 is an illustration of a portion of the leading edge of an aircraft wing 104 comprising a plurality of heaters 202, 204, 206, 208, 210, 212, 214, which form part of the present invention. The heaters are located under the surface (hence shown dashed) of the wing, but are in thermal contact with the surface of the wing. Seven heaters (not to scale) are shown in this figure, although it would be clear to the skilled reader that there could be more or fewer regions than indicated. The heaters 202 to 214 are arranged such that a master heater 202 is located on the leading edge of the structure 104, with secondary or slave heaters 204, 206, 208, 210 aft of the master heater 202 on an upper surface of the structure 104 in a direction of the airflow that would impinge on the surface. Secondary or slave heaters 212 and 214 are arranged aft of and beneath the structure in a direction of the airflow that would impinge on the surface.

FIG. 3 is a cross-section 300 of the structure of an aircraft wing section. The figure shows the leading edge 302 of the wing in cross-section and an approximation of the airflow 304 over the wing whilst in flight. The wing includes an erosion shield 306, typically a stiff, erosion-resistant aluminium shield, a dielectric (insulator) 308, a heater layer 310 (in which the heaters 202 to 214 are located), another dielectric 312, and a temperature sensor 314. Only one temperature sensor is shown for clarity, although each heater 202 to 214 is in thermal contact with its own temperature sensor). The layers 306, 308, 310, 312 are much thinner than as shown, forming a thin sandwich at the edge of the wing section.

The main wing section 302 is formed from any appropriate material, such as composite materials that comprise a plurality of layers of stiff material bound together with glue. Composite materials have a good ratio of strength to weight, but are susceptible to failure by delamination (when the glue melts) at a relatively low temperature. Therefore care needs to be taken to avoid 'overshoot' (overheating) of the heater.

Figure 6:
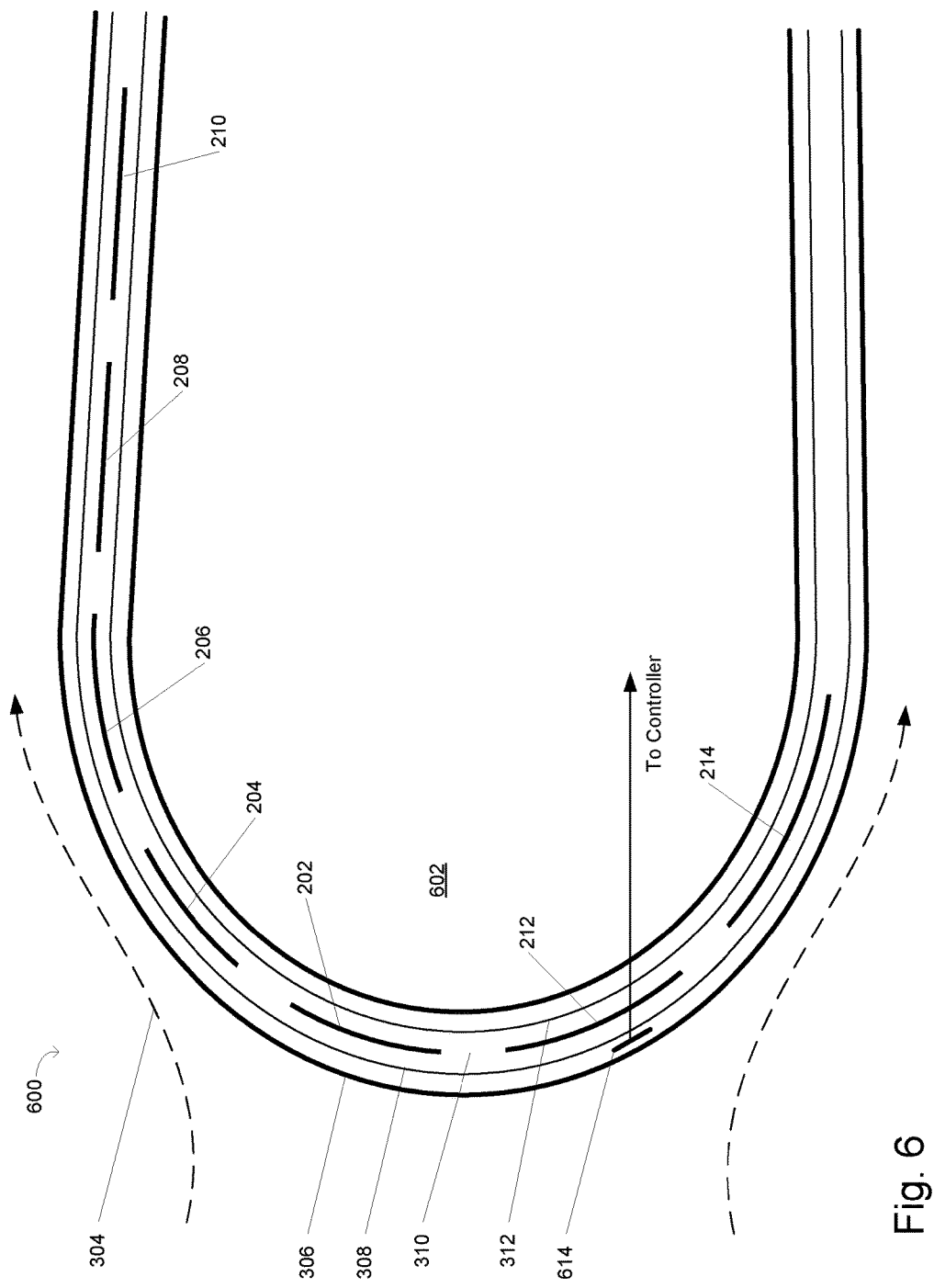
FIG. 6 is a cross-section of the structure of an aircraft wing section in an alternative arrangement.

It will be appreciated that a similar arrangement may be provided on other exposed parts of the aircraft structure (such as on propeller leading edges or on engine inlets, for example). It will also be appreciated that the temperature sensor 314 may be located between the heater layer 310 and the erosion shield 306, as shown in FIG. 6 (discussed below).

FIG. 4 is an illustration of thermal resistances and thermal capacitances of the wing section of FIG. 3.

The thermal resistances (degree of thermal insulation) and thermal capacitances (heat capacity) are illustrated using electrical equivalents, with heat flow corresponding to electrical current and temperatures corresponding to voltages. In this representation, the heat generated by the heater mat is represented by a current source $Q_{HEAT\ INPUT}$ and the temperature sensor 314 of FIG. 3 is represented as a voltage measurement. Each of the layers has an associated thermal capacity (which may be negligible) and the thermal resistance of each layer is also shown. The heat loss at the breeze surface (the interface with the air impinging on the wing), $Q_{HEAT\ LOSS\ (BREEZE)}$, and the heat loss into the interior of the wing, $Q_{HEAT\ LOSS\ (INTERIOR)}$, are also indicated (as currents flowing out of the thermal circuit). The heat loss $Q_{HEAT\ LOSS\ (INTERIOR)}$ into the interior of the structure is considerably less than the heat loss $Q_{HEAT\ LOSS\ (BREEZE)}$ through the erosion shield (by design).

The thermal properties of the wing section during normal ice protection or detection conditions (during flight) will now be described in more detail.

FIG. 5 is a graph illustrating the variation of temperature over distance within the wing section of FIG. 3. The temperature 502 is plotted from the left hand side 504, where large amounts of heat flow through the erosion shield, to the right hand side 506, where heat is slowly lost into the wing structure. The gradient of the curve 502 is equivalent to the thermal gradient (although not drawn to scale).

The heater Temperature $T_{HEATER}$, the temperature sensor temperature $T_{SENSOR}$ and the erosion shield temperature $T_{ES}$ are indicated on the temperature curve 502. The temperature sensor temperature $T_{SENSOR}$ is approximately equal to the heater Temperature $T_{HEATER}$ because of the shallow thermal gradient flowing into the structure 506. The erosion shield temperature $T_{ES}$ is quite different, however, because of the steep temperature gradient flowing out of the wing 504. In accordance with the electrical analogy in FIG. 5, the temperature T is substitutable for a voltage, and a corresponding current can be derived from the gradient of the curve 502.

As such, the temperature of the surface can be determined from the known properties of the component parts of the surface, the known amount of power supplied to the heater, and from a measurement of the temperature sensor adjacent the heater.

FIG. 6 is a cross-section of the structure of an aircraft wing section in an alternative arrangement to that shown in FIG. 3. In FIG. 6, the temperature sensor 614 is located between the heater layer 310 and the erosion shield 306, as shown in FIG. 6. Again, only one temperature sensor 614 is shown. Preferably each heater 202 to 214 is in thermal contact with a respective temperature sensor.

FIG. 7 is an illustration of thermal resistances and thermal capacitances of the wing section of FIG. 6. The principles remain the same as in FIG. 4, although it should be noted that the Temperature Sensor is now between the heater and the erosion shield.

Similarly, FIG. 8 shows a graph illustrating the variation of temperature over distance within the wing section of FIG. 6. The temperature 802 is plotted from the left hand side 804, where large amounts of heat flow through the erosion shield, to the right hand side 806, where heat is slowly lost into the wing structure. The gradient of the curve 802 is equivalent to the thermal gradient (although not drawn to scale).

The heater Temperature $T_{HEATER}$, the temperature sensor temperature $T_{SENSOR}$ and the erosion shield temperature $T_{ES}$ are indicated on the temperature curve 802. Since the temperature sensor $T_{SENSOR}$ is located between the heater layer and the erosion shield, the temperature of the temperature sensor $T_{SENSOR}$ is quite different to the heater Temperature $T_{HEATER}$ due to the steep temperature gradient flowing out of the wing 804.

Similarly, the erosion shield temperature $T_{ES}$ is quite different because of the steep temperature gradient flowing out of the wing 804. In accordance with the electrical analogy in FIG. 7, the temperature T is substitutable for a voltage, and a corresponding current can be derived from the gradient of the curve 802.

As such, the temperature of the surface can be determined from the known properties of the component parts of the surface, the known amount of power supplied to the heater, and from a measurement of the temperature sensor.

The method of detecting the presence of water or ice on a surface of a structure (for example the wing structure described above) will now be described.

As well as each of the heaters 202 to 214 being in thermal contact with the surface of the structure (each heater therefore heats a respective region of the surface of the structure), each of the heaters 202 to 214 is electrically coupled to a controller for controllably supplying power to each of the heaters. The controller receives temperature sensor signals from each of the temperature sensors (each temperature sensor being thermally coupled to a respective heater. As such, the temperature sensor provides a measure of the heated region close to the heater, which is indicative of the heater temperature, and the surface temperature of the structure may be inferred or calculated as described above).

The method will first be described with reference to a single heater (for example heater 202 on the leading edge of the wing), since in its most basic form only a single heater is required to detect the presence of water or ice on the surface of the wing.

The heater 202 is supplied with a first power, where the first power is sufficient to heat a surface of the structure at the first region. Preferably, the first power applied to the heater is controlled such that the surface temperature is sufficiently high enough to cause evaporation of water or ice in contact with the surface of the structure at the first region. Effectively, a desired master RTD temperature ($T_{set}$) is set and the controller controls the power applied to the mat to achieve this temperature (this can be achieved for example either by switching the applied voltage on and off (Pulse Width Modulation) and/or modifying the applied voltage). The controller uses the temperature sensor signal to control the power applied to the mat to achieve the desired $T_{set}$ (the surface temperature being calculated as discussed below). $T_{set}$ is a dynamic value which is set as high as possible to:
 maximize surface water evaporation (minimizing runback); and
 minimize the effect of measurement errors
 However, the value of $T_{set}$ is limited by:
 the maximum temperature to which any part of the wing or heater assembly can be taken to without risk of failure (for example delamination)
 the maximum power that may be drawn from the power supply (or an airplane-allocated power budget)

In practice, $T_{set}$ is controlled such that $T_{master\_surface}$ is greater than the ambient temperature of the environment to which the structure is exposed. Preferably, $T_{set}$ is controlled such that $T_{master\_surface}$ is greater than 30° C., 40° C., 50° C. or 60° C. above an ambient temperature. More preferably, $T_{set}$ is controlled such that $T_{master\_surface}$ is greater than 50° C. above an ambient temperature.

With regards to the surface temperature, the higher the difference between the heated surface temperature and the ambient temperature:
 the greater the sensitivity to detecting low water concentrations;
 the more accuracy in the determination of the impingement profile (see below).

Whilst the system will work for temperature differences of less than 50° C., the performance of the system may be less than optimal. There will be a temperature difference at which the system will not be fit for purpose, however this is not a fixed value, as it is dependent on ambient conditions, the accuracy of the external data the detector is receiving and the sensitivity of the structure to icing. As such, the preferred approach is to maintain the temperature difference as high as possible without compromising potential overheat conditions or exceeding power budgets. Where the system cannot maintain this difference, it will be in high water content conditions—which the system will correctly detect.

In practice, in dry or low water content conditions the system may maintain the leading edge heater temperature sensor in the region of 100° C. to 110° C. (dictated by overheat protection needs). Typically, the surface temperature would then be in the range 60° C. (high airspeed, high air density) to 80° C. (low airspeed, low air density). In high water content conditions the heater (and hence the surface) temperature would be allowed to drop because the total power consumption would become too high. As discussed above, in the case where there is high water content, this will be detected by the system.

The controller calculates a power consumed by the first heater ($P_{act}$) at the first power. This may be calculated from the measurements of the current flowing from the controller to drive the heater and the (known) electrical resistance of the heater.

The controller also calculates a first surface temperature ($T_{surf}$) of the surface of the structure at the first region—this calculation is also used to control the heat output of other regions. The controller may use the known thermal properties of the heater assembly (i.e. the heater and the structure), the power applied, and the temperature sensor signal.

The controller also calculates a reference power ($P_{dry}$) for applying to the first heater to achieve the first surface temperature ($T_{surf}$) at the surface of the structure at the first region if the first region of the structure was subjected to an environmental condition that was substantially devoid of water (i.e. if the air was dry in the prevailing conditions). How this is calculated will be discussed later.

The controller then calculates a power difference ($P_{diff}$) between the power consumed by the first heater at the first power and the reference power ($P_{dry}$), which enables the presence of water or ice on the surface of a structure at the first region to be detected by comparing $P_{diff}$ to a power threshold value. If $P_{diff}$ is greater than the power threshold value, the presence of water or ice on the surface of the structure is inferred. (For high LWC (liquid water content) a straight comparison would be sufficient. However, for low LWC use of an integrator may be required, which would indicate when an output of the integrator exceeds a threshold).

$P_{act}$ will be greater than $P_{dry}$ if the impinging air is wet, due to the extra energy required to heat or evaporate incident water. $P_{diff}$ is therefore a measure of the quantity of impinging water on each zone, from which an estimate of the impinging Liquid Water Content (LWC) and effective accretion rate can be made.

If $P_{diff}$ is greater than a power threshold value or an accumulation over time of $P_{diff}$ is greater than a power threshold value for the master region associated with the master heater 202, then a 'not dry' condition is inferred. If, in addition, the environmental conditions are conducive to icing (e.g. TAT—Total Air Temperature—is less than or close to 0° C.), an 'icing' condition is inferred (i.e. a condition in which ice is likely to accumulate on the structure), and may be indicated to a pilot and/or used to control an ice protection system on the aircraft automatically.

Instead of calculating a difference between the power required to heat the surface of the structure to the desired temperature and the power required to heat the surface of the structure to the same temperature when the structure is in an environment devoid of water, the method may simply compare the two powers, and infer the presence of water if the power required to heat the surface of the structure is greater than the power required to heat the surface of the structure to the same temperature when the structure is in an environment devoid of water.

Furthermore, instead of calculating a difference, the method may calculate a ratio of the two powers ($P_{act}/P_{dry}$). In such a case, a ratio of greater than 1 would infer that there is water or ice on the surface of the structure.

The method will now be described with reference to a plurality of heaters (for example one or more of heaters 202 to 214).

As with the above method, the heater 202 is supplied with a first power, where the first power is sufficient to heat a surface of the structure at the first region. As above, the master heater 202 is controlled such that the temperature sensor at the first region achieves the desired temperature $T_{set}$.

The controller also applies a respective power to each of the secondary or slave heaters 204, 206, 208, 210, 212, 214. In this case, the controller controls the application of power to each of the secondary heaters 204 to 214 such that the temperature at the surface of each of the regions associated with the secondary heaters is substantially the same as the surface temperature ($T_{surf}$) of the region associated with the first or master heater 202.

The secondary or slave heaters are controlled in this way in order to try to achieve a uniform temperature over the entire outer surface of the structure. Maintaining a uniform temperature across the erosion shield enables errors in the power difference calculations to be reduced. The thermal conductivity of the (normally aluminium) surface is high and if there are temperature variations from the surface of one heated region to another then there is significant heat leakage between regions, which result in large errors in the power difference calculations described below.

As above, the controller also calculates a power consumed by each of the secondary heaters ($P_{act}$) at the respective power. This may be calculated from the measurements of the current flowing from controller to drive the heater and the (known) electrical resistance of the heater.

The controller also calculates a surface temperature ($T_{surf}$) of the surface of the structure at the region associated with the respective secondary heater. The controller may use the known thermal properties of the heater assembly (i.e. the heater and the structure), the power applied, and the temperature sensor signal to calculate the surface temperature.

The controller also calculates a reference power ($P_{dry}$) for applying to each of the secondary heaters to achieve the respective surface temperature ($T_{surf}$) at the surface of the structure at the respective region if the respective region of the structure was subjected to an environmental condition that was substantially devoid of water (i.e. if the air was dry in the prevailing conditions). How this is calculated will be discussed later.

The controller then calculates a power difference ($P_{diff}$) for each of the secondary heaters between the power consumed by the respective secondary heater at the respective power and the reference power ($P_{dry}$), which enables the presence of water or ice on the surface of a structure at the respective region to be detected by comparing $P_{diff}$ for each secondary region to a power threshold value. As above, if $P_{diff}$ is greater than the power threshold value, the presence of water or ice is inferred.

As above, $P_{act}$ will be greater than $P_{dry}$ if the impinging air is wet, due to the extra energy required to heat or evaporate incident water. Furthermore in this method where there are a plurality of heated regions, $P_{diff}$ may actually be scaled to be a Power Density Difference so that direct comparisons can be made between regions (the effective heated surface areas of each region will be different).

As above, if $P_{diff}$ is greater than a power threshold value or an accumulation over time of $P_{diff}$ is greater than a power threshold value for the master region(s) then a 'not dry' condition is inferred.

If $P_{diff}$ is greater than a threshold or an accumulation over time of $P_{diff}$ is greater than a threshold for any of the secondary or slave heaters then a 'not dry' condition is inferred for the applicable regions.

If $P_{diff}$ is negative, there are two possibilities:

1) For a region aft of a region that is 'not dry' the aft region is dry and the forward region does not have water impinging all the way to the back of that region. As a result, either a temperature gradient forms across the forward region such that the rear of the forward region is hotter than the estimated surface temperature and heat leaks on to the aft region via the erosion shield such that the aft region does not need to supply as much power to maintain its surface temperature as it would in dry conditions, hence $P_{diff}$ becomes negative. Or, the presence of water in a forward region disrupts the aft airflow, making it turbulent, thereby increasing the local thermal conductance and hence decreasing the power required to maintain the surface temperature.

2) For a region aft of a region that is 'dry', laminar flow over the mat has turned into turbulent flow, thereby increasing the local thermal conductance; this could be an indication of a stall or impending stall—particularly if it is accompanied by a shift in the stagnation point (see below).

As discussed with reference to the single-heater version, the presence of water or ice may be inferred by comparing the power required to heat the surface of the structure to the desired temperature and the power required to heat the surface of the structure to the same temperature when the structure is in an environment devoid of water, or may be inferred from a ratio of the two powers.

As discussed above, the method requires a calculation of the reference power ($P_{art}$), which is the power required to achieve the respective surface temperature ($T_{surf}$) at the surface of the structure at the respective region if the respective region of the structure was subjected to an environmental condition that was substantially devoid of water (i.e. if the air was dry in the prevailing conditions).

In its broadest form, ($P_{dry}$) is a sum of conductive, convective and radiative heat losses. The conductive and convective heat losses are dominated by:

The temperature drop at the breeze surface ($T_{surf}$-Total Air Temperature (TAT)); multiplied by The mass of air flowing past the mat, being proportional to the free-stream airspeed (V) times the Air Density ($\rho$). The Air Density can be calculated from Pressure Altitude and Static Air Temperature (SAT); multiplied by The heat transfer coefficient of the surface to the air (K).

Conductive heat losses through the wing are small in comparison (provided that the erosion shield surface temperature can be kept largely uniform in the heated region, the temperature sensors are sufficiently far away from unheated regions and there is good thermal insulation at the back of the heater) and are not changed much by wet or dry conditions and can be ignored.

The free-stream airspeed, SAT, TAT and Pressure Altitude can be obtained from data from other aircraft systems.

There are 3 more correction factors that may be applied:

The stagnation point in front of the leading edge will move with: a) the angle that the detector makes with the incident airflow, which is a function of Angle of Attack (AoA) and, if the detector is mounted on a movable slat, the slat position; and b) flap and spoiler positions, thereby changing the heat transfer coefficient K. This data can be inferred and corrected for either from information obtained from other aircraft systems or from power and/or temperature gradients for the zones closest to the leading edge.

The asymmetric cooling effects of cross-winds when the aircraft heading is not coincident with the direction of airflow. This information can be obtained either from other aircraft systems or by positioning 2 detectors in symmetrical positions on both wings and correcting for the asymmetry in power losses from the 2 detectors.

Friction effects mean that, firstly, TAT, as measured by other systems, will not exactly match the temperature of the unheated leading edge (meaning that a correction proportional to the square of the free-stream airspeed should be made), and secondly, affect the thermal conductance of the air (meaning a correction proportional to the mean temperature of the boundary layer should be made to K).

A radiative loss correction (proportional to ($T_{surf}^4 - SAT^4$)) could also be applied, but this should be small compared to the above terms.

In preferred embodiments, $P_{dry}$ may be calculated using a relationship of the form:

$$P_{dry} = K(T_{surface} - TAT)V\rho$$

where:

K is the heat transfer coefficient of the surface to the air
$T_{surface}$ is a surface temperature at a region
TAT is the total air temperature of the environment surrounding the structure
V is the free-stream airspeed
$\rho$ is the density of the air surrounding the structure The density ($\rho$) of the air surrounding the structure may be determined using a relationship of the form:

$$\rho = \rho_0 T_0 \frac{e^{(-altitude/ref\_alt)}}{SAT}$$

Where:

$\rho_0$ is the air density at standard Temperature and Pressure
$T_0$ is standard Temperature
altitude is the altitude of the structure (in ft)
ref_alt is a reference altitude (in ft; for example in the region of 27627)
SAT is the Static Air Temperature.

Alternatively, the density ($\rho$) of the air surrounding the structure may be determined using a relationship of the form:

$$\rho = \rho_0 \frac{PT_0}{P_0 SAT}$$

Where:

$\rho_0$ is the air density at standard Temperature and Pressure
$T_0$ is standard Temperature
P is the Static Air Pressure
$P_0$ is the Standard Air Pressure
SAT is the Static Air Temperature.

In the embodiments comprising a plurality of heaters (202 to 214), an impingement profile can be generated from the different $P_{diff}$ calculations across all of the heaters, from which a measure of how far back on the surface water is impinging can be determined.

Figure 9:
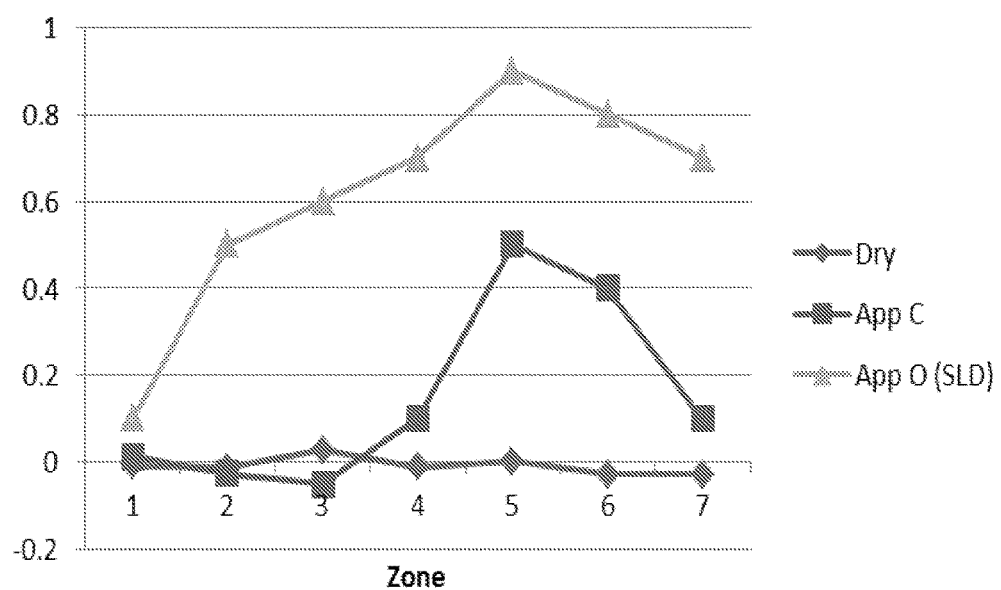
FIG. 9 shows an example impingement profile.

FIG. 9 shows a calculated example impingement profile for dry air conditions, 'normal' icing conditions (Appendix C) and SLD—Supercooled Large Droplet (Appendix O) conditions. In this figure, zone 5 is a region at the leading edge (i.e. the master or first heater), zone 1 is aft-most on the upper surface and zone 7 is aft-most on the lower surface.

As can be seen, SLD conditions impinge much further aft than 'normal icing' conditions. As such, the present invention may be used to identify SLDs impinging on the surface easily, and provide a suitable indication. If the measure of how far back the impingement occurs exceeds a limit (corresponding to the limit beyond which the wing surface is unprotected) then an indication that ice accretion is occurring in an unprotected area can be generated. Such a limit can for example be dependent on the distance or number of regions aft of the leading edge region (i.e. master region).

In icing crystal conditions the impingement profile will look similar to the dry conditions (ice crystals bounce off and do not stick).

Figure 10:
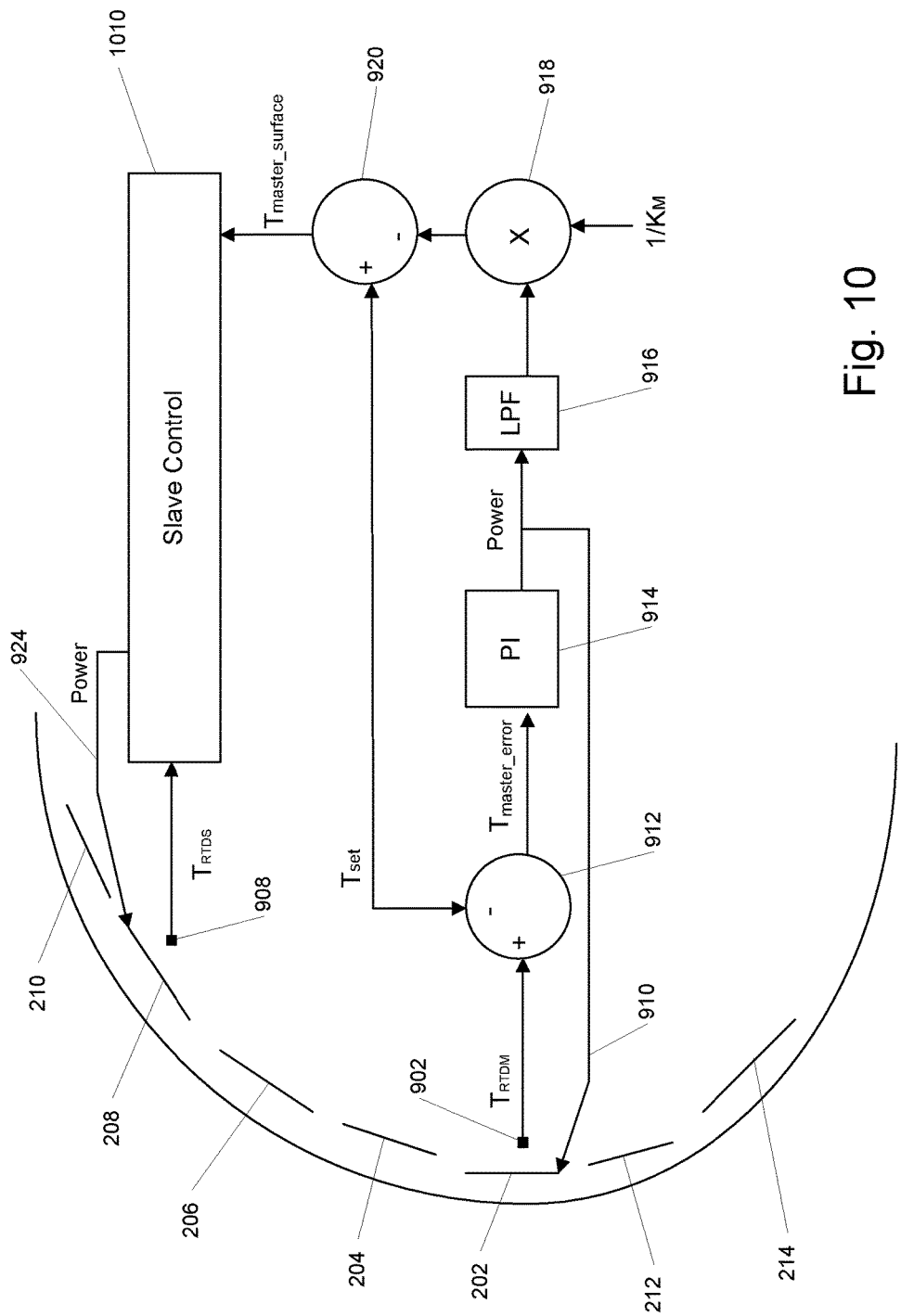
FIG. 10 is an illustration of part of a control system.

FIG. 10 is an illustration of a simplified control scheme. The figure shows the master controller 914 for controlling the master or first heater 202, and one of the secondary or slave controllers 1010 for controlling one of the secondary heaters (208 in the case as shown). Additional secondary controllers for the remaining secondary heaters are not shown for the sake of clarity.

The master controller 914 is preferably a proportional and integral controller. A temperature sensor 902 provides a temperature sensor signal, from which is subtracted the desired temperature $T_{set}$. This produces an error signal $T_{master\_error}$, which is fed into the master controller 914. Master controller 914 then outputs a proportional drive signal depending on how large the error signal is to drive the heater to achieve the desired temperature.

The power output drives the heater (via connection 910) and provides a power signal to a low pass filter 916, which is used to feed a portion of this signal to the secondary or slave controller 1010. The low pass filtered power signal is multiplied by the reciprocal of the thermal conductance of the master region ($K_M$) and subtracted from the desired temperature $T_{set}$. This provides a calculation of the temperature at the surface of the master region $T_{master\_surface}$. Secondary or slave controller 1010 uses $T_{master\_surface}$, and the temperature sensor 908 signal to generate a drive signal 924 to drive the secondary heater 208 (as discussed below).

Figure 11:
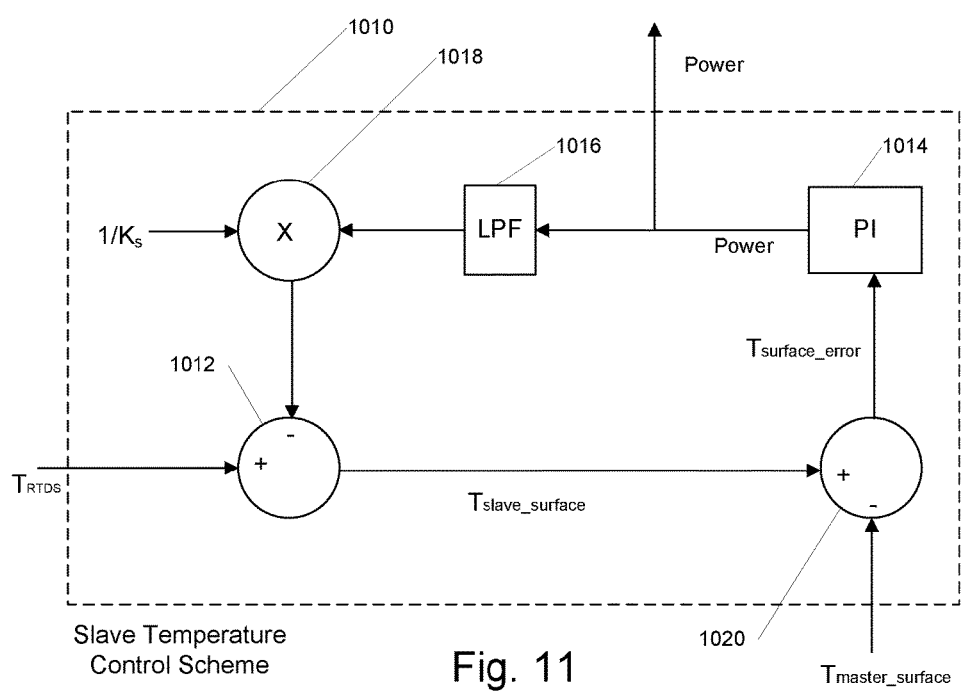
FIG. 11 is an illustration of a further part of the control system of FIG. 10.

The operation of the secondary or slave controller 1010 will now be described with reference to FIG. 11.

The secondary controller 1014 is preferably a proportional and integral controller. The secondary controller 1014 receives an error signal $T_{surface\_error}$, which is a measure of the error of the temperature determined at the surface compared to the desired surface temperature. Secondary controller 1014 then outputs a proportional drive signal depending on how large the error signal is to drive the secondary heater 208 to achieve the desired temperature. As discussed above, each of the secondary controllers control the power applied to the heaters to achieve a surface temperature at the respective region that is substantially equal to the temperature at the surface of the master region. $T_{surface\_error}$ is generated by subtracting the received $T_{master\_surface}$ calculation from the determined $T_{slave\_surface}$, which is the determined surface temperature at the secondary or slave region in thermal contact with the heater 208, using the subtractor 1020. $T_{slave\_surface}$ is generated by multiplying the output power drive signal from the controller 1014 and the reciprocal of the thermal conductance ($K_s$) of the secondary region associated with the heater 208 using multiplier 1018, and subtracting that product from the temperature sensor signal $T_{RTDS}$ from the temperature sensor 908 using subtractor 1012. As discussed above, the temperature sensor may be used in the calculation of the surface temperature (depending on the measurement of the temperature sensor and the known thermal properties of the structure).

Although the present invention has been described hereinabove with reference to specific embodiments, the present invention is not limited to the specific embodiments and modifications will be apparent to a skilled person in the art which lie within the scope of the claims. Any of the embodiments described hereinabove can be used in any combination with one or more of the other embodiments.

The invention claimed is:

1. A method of controlling de-icing of a surface of a structure, the structure being exposable to an impinging airflow, the method comprising the steps of:
    supplying a first heater with a first power, the first heater being in thermal contact with a first region of a structure exposable to an impinging airflow, the first power being sufficient to heat a surface of the structure at the first region;
    supplying each of one or more second heaters with a respective power, each of the one or more second heaters being in thermal contact with a respective region of the structure exposable to an impinging airflow, each of the respective powers being sufficient to heat a surface of the structure at the respective region; and
    detecting the presence of water or ice on the surface of a structure at a respective region by comparing a power consumed by a respective heater to achieve a temperature at the surface of the structure at the respective region with a reference power for the respective heater, wherein the reference power is a power for applying to the respective heater to achieve the same temperature at the surface of the structure at the respective region if the respective region of the structure was subjected to an environmental condition that was substantially devoid of water, and
    wherein water or ice is detected when the power consumed by the respective heater is greater than the reference power; and
    controlling one or more of the first and second heaters in response to the detection of ice or water on the surface of the structure to de-ice the surface of the structure.

2. A method according to claim 1, comprising calculating a surface temperature, comprising:
    measuring a temperature of the first or second heaters; and
    calculating the surface temperature from the temperature of the first or second heater, the power applied to the first or second heater, and at least one thermal resistance between the first or second heater and the surface of the structure.

3. A method according to claim 1, further comprising:
    measuring a temperature of the first heater; and
    controlling the first power applied to the first heater using the measured temperature of the heater.

4. A method according to claim 3, wherein the first power applied to the first heater is controlled such that the surface temperature is sufficient to cause evaporation of water or ice in contact with the surface of the structure at the first region.

5. A method according to claim 1, further comprising:
    controlling the respective power applied to each of the second heaters such that the surface temperature at the respective region is substantially the same as the surface temperature of the first region.

6. A method according to claim 1, wherein the first region of a structure is located on a leading edge of the structure, and wherein one of the respective regions thermally coupled to one of the second heaters is adjacent and aft of the first region in a direction of an impinging airflow on the structure.

7. A method according to claim 6, wherein a further region in thermal contact with another of a respective one of the second heaters is adjacent and aft of the one of the respective regions in a direction of an impinging airflow on the structure.

8. A method according to claim 6, further comprising:
    identifying a region aft of the first region having water or ice detected thereon; and
    generating a signal if a distance of the identified region aft of the first region is greater than a threshold distance.

9. A method according to claim 1, wherein the first surface temperature is greater than or equal to 50° C. above a temperature of the environment to which the structure is exposed.

10. A method according to claim 1, comprising calculating the reference power, comprising:
    determining a temperature drop at the surface of the structure;
    determining a mass of air flowing past a region of the structure with which the first or second heaters is in thermal contact;
    calculating the reference power depending on the temperature drop at the surface of the structure and the mass of air flowing past the region of the structure.

11. A method according to claim 10, wherein determining a temperature drop at the surface of the structure comprises:
    calculating a surface temperature of the surface at a region;
    measuring a total temperature of the environment surrounding the structure; and subtracting the total temperature of the environment surrounding the structure from the surface temperature.

12. A method according to claim 10, wherein determining a mass of air flowing past a region of the structure comprises:
   measuring an airspeed of the structure;
   calculating a density of the air flowing past the structure using a measurement of the altitude of the structure, or air pressure, and a calculation of the static air temperature; and
   calculating the mass of air flowing past a region of the structure using the airspeed and density.

13. A method according to claim 10, wherein the reference power is calculated using the relationship:

$$P = K(T_{surface} - TAT)V\rho$$

where:
K is the heat transfer coefficient of the surface to the air
$T_{surface}$ is a surface temperature at a region
TAT is the total air temperature of the environment surrounding the structure
V is the free-stream air speed
$\rho$ is the density of the air surrounding the structure.

14. A method according to claim 13, wherein the density of the air surrounding the structure is determined by the relationship:

$$\rho = \rho_0 T_0 \frac{e^{(-altitude/ref\_alt)}}{SAT}$$

Where:
$\rho_0$ is the air density at standard Temperature and Pressure
$T_0$ is the standard Temperature
altitude is the altitude of the structure (in ft)
ref_alt is a reference altitude (in ft)
SAT is the Static Air Temperature.

15. A method according to claim 13, wherein the density of the air surrounding the structure is determined by the relationship:

$$\rho = \rho_0 \frac{PT_0}{P_0 SAT}$$

where:
$\rho_0$ is the air density at standard Temperature and Pressure
$T_0$ is standard Temperature
P is the Static Air Pressure
$P_0$ is the Standard Air Pressure
SAT is the Static Air Temperature.

16. A method of detecting an icing condition in which ice may form on a structure exposable to an impinging airflow, the method comprising:
   detecting the presence of water on the surface of a structure exposable to an impinging airflow according to claim 1;
   detecting an air temperature of the environment external to the structure;
   detecting an icing condition dependent on the detection of the presence of water on the surface of the structure and the air temperature being substantially at or below 10° C.

17. A method according to claim 16, further comprising generating a signal if an icing condition is detected.

18. Apparatus for controlling de-icing of a surface of a structure, the structure being exposable to an impinging airflow, the apparatus comprising:
   a first heater thermally coupleable to a first region of structure exposable to an impinging airflow,
   a first temperature sensor thermally coupled to the first heater for sensing the temperature of the first heater and for outputting a first temperature signal;
   one or more second heaters thermally coupleable to a respective region of the structure,
   for each of the one or more second heaters, a respective temperature sensor thermally coupled thereto for sensing the temperature of the respective second heater and for outputting a respective temperature signal;
   a controller coupled to the first heater, first temperature sensor, each of the one or more second heaters and each of the respective temperature sensors and for controllably applying power to the first heater and one or more second heaters, the controller being configured to:
      supply the first heater with a first power, the first power being sufficient to heat a surface of the structure at the first region;
      supply each of the one or more second heaters with a respective power, the respective power being sufficient to heat a surface of the structure at the respective region; and
      detect the presence of water or ice on the surface of a structure at a respective region by comparing the power consumed by a respective heater to achieve a temperature at the surface of the structure at the respective region with a reference power for the respective heater, and
      controlling one or more of the first and second heaters in response to the detection of ice or water on the surface of the structure to de-ice the surface of the structure
   wherein the reference power is a power for applying to the respective heater to achieve the same temperature at the surface of the structure at the respective region if the respective region of the structure was subjected to an environmental condition that was substantially devoid of water, and wherein the controller detects the presence of water or ice when the power consumed by the respective heater is greater than the reference power.

19. Apparatus according to claim 18, wherein the controller is configured to calculate the surface temperature by:
   receiving the temperature signal; and
   calculating the surface temperature from the temperature signal, the power applied to the first or second heaters, and at least one thermal resistance between the first or second heaters and the surface of the structure.

20. Apparatus according to claim 18, wherein the controller is configured to control the first power applied to the first heater using the first temperature signal.

21. Apparatus according to claim 20, wherein the first power applied to the first or second heaters is sufficient to cause evaporation of water or ice in contact with the surface of the structure at the first region.

22. Apparatus according to claim 18, wherein the first region of a structure is located on a leading edge of the structure, and wherein one of the respective regions thermally coupled to one of the second heaters is adjacent and aft of the first region in a direction of an impinging airflow on the structure.

23. Apparatus according to claim 22, wherein a further region in thermal contact with another of a respective one of the second heaters is adjacent and aft of the one of the respective regions in a direction of an impinging airflow on the structure.

24. Apparatus according to claim 18, wherein the controller is configured to control the power applied to each of the one or more second heaters such that the respective surface temperature is substantially the same as the surface temperature of the first region.

25. Apparatus according to claim 18, wherein the first surface temperature is greater than or equal to 50° C. above a temperature of the environment to which the structure is exposed.

26. Apparatus according to claim 18, wherein the first or second heaters is disposed in a layer between the temperature sensor and a surface of the structure.

27. Apparatus according to claim 18, wherein the temperature sensor is disposed in a layer between the first or second heaters and a surface of the structure.

28. Apparatus according to claim 18, wherein the controller is configured to calculate the reference power by:
    determining a temperature drop at the surface of the structure;
    determining a mass of air flowing past a region of the structure with which the first or second heaters is in thermal contact;
    calculating the reference power depending on the temperature drop at the surface of the structure and the mass of air flowing past the region of the structure.

29. Apparatus according to claim 28, wherein the controller is configured to determine a temperature drop at the surface of the structure by:
    calculating a surface temperature of the surface at a region;
    measuring a total temperature of the environment surrounding the structure; and
    subtracting the total temperature of the environment surrounding the structure from the surface temperature.

30. Apparatus according to claim 28, wherein the controller is configured to determine a mass of air flowing past a region of the structure by:
    measuring an airspeed of the structure;
    calculating a density of the air flowing past the structure using a measurement of the altitude of the structure, or air pressure, and a calculation of the static air temperature; and
    calculating the mass of air flowing past a region of the structure using the airspeed and density.

31. Apparatus according to claim 28, wherein the controller calculated the reference power using the relationship:

$$P = K(T_{surface} - \text{TAT})V\rho$$

where:
K is the heat transfer coefficient of the surface to the air
$T_{surface}$ is a surface temperature at a region
TAT is the total air temperature of the environment surrounding the structure
V is the free-stream air speed
$\rho$ is the density of the air surrounding the structure.

32. Apparatus according to claim 31, wherein the density of the air surrounding the structure is determined by the relationship:

$$\rho = \rho_0 T_0 \frac{e^{(-altitude/ref\_alt)}}{SAT}$$

Where:
$\rho_0$ is the air density at standard Temperature and Pressure
$T_0$ is the standard Temperature
altitude is the altitude of the structure (in ft)
ref_alt is a reference altitude (in ft)
SAT is the Static Air Temperature.

33. Apparatus according to claim 31, wherein the density of the air surrounding the structure is determined by the relationship:

$$\rho = \rho_0 \frac{PT_0}{P_0 SAT}$$

where:
$\rho_0$ is the air density at standard Temperature and Pressure
$T_0$ is standard Temperature
P is the Static Air Pressure
$P_0$ is the Standard Air Pressure
SAT is the Static Air Temperature.

34. A controller for controlling the de-icing of a surface of a structure, the structure being exposable to an impinging airflow, the controller comprising:
    an output adapted to supply power to a first heater, the first heater being thermally coupleable to a first region of structure exposable to an impinging airflow,
    an input adapted to receive a first temperature sensor signal from a first temperature sensor thermally coupleable to the first heater for sensing the temperature of the first heater;
    one or more second outputs adapted to supply power to respective one or more second heaters, the one or more second heaters being thermally coupleable to a respective region of the structure;
    one or more second inputs adapted to receive respective temperature sensor signals from respective one or more second temperature sensors, each of the one or more second temperature sensors being thermally coupleable to a respective second heater, and each of the one or more second temperature sensors for sensing the temperature of the respective heaters;
the controller being configured to:
    supply a first power to a first heater, the first power being sufficient to heat a surface of the structure at the first region;
    supply each of the one or more second heaters with a respective power, the respective power being sufficient to heat a surface of the structure at the respective region; and
    detect the presence of water or ice on the surface of a structure at a respective region by comparing the power consumed by a respective heater to achieve a temperature at the surface of the structure at the respective region with a reference power for the respective heater, wherein the reference power is a power for applying to the respective heater to achieve the same temperature at the surface of the structure at the respective region if the respective region of the structure was subjected to an environmental condition that was substantially devoid of water, and
    wherein the controller detects the presence of water or ice when the power consumed by the respective heater is greater than the reference power; and
    controlling one or more of the first and second heaters in response to the detection of ice or water on the surface of the structure to de-ice the surface of the structure.

35. A controller according to claim 34, wherein the controller is configured to calculate the surface temperature by:
receiving the temperature sensor signal; and
calculating the surface temperature from the temperature sensor signal, the power applied to the first or second heaters, and at least one thermal resistance between the first or second heaters and the surface of the structure.

36. A controller according to claim 34, wherein the controller is configured to control the first power applied to the first heater using the first temperature signal.

37. A controller according to claim 36, wherein the first power applied to the heater is sufficient to cause evaporation of water or ice in contact with the surface of the structure at the first region.

38. A controller according to claim 34, wherein the first region of a structure is located on a leading edge of the structure, and wherein one of the respective regions thermally coupled to one of the second heaters is adjacent and aft of the first region in a direction of an impinging airflow on the structure.

39. A controller according to claim 38, wherein a further region in thermal contact with another of a respective one of the second heaters is adjacent and aft of the one of the respective regions in a direction of an impinging airflow on the structure.

40. A controller according to claim 34, wherein the controller is configured to control the power applied to each of the one or more second heaters such that the respective surface temperature is substantially the same as the surface temperature of the first region.

41. A controller according to claim 34, wherein the first surface temperature is greater than or equal to 50° C. above a temperature of the environment to which the structure is exposed.

42. A controller according to claim 34, wherein the controller is configured to calculate the reference power by:
determining a temperature drop at the surface of the structure;
determining a mass of air flowing past a region of the structure with which the first or second heaters is in thermal contact;
calculating the reference power depending on the temperature drop at the surface of the structure and the mass of air flowing past the region of the structure.

43. A controller according to claim 42, wherein the controller is configured to determine a temperature drop at the surface of the structure by:
calculating a surface temperature of the surface at a region;
measuring a total temperature of the environment surrounding the structure; and
subtracting the total temperature of the environment surrounding the structure from the surface temperature.

44. A controller according to claim 42, wherein the controller is configured to determine a mass of air flowing past a region of the structure by:
measuring an airspeed of the structure;
calculating a density of the air flowing past the structure using a measurement of the altitude of the structure, or air pressure, and a calculation of the static air temperature; and
calculating the mass of air flowing past a region of the structure using the airspeed and density.

45. A controller according to claim 42, wherein the controller calculated the reference power using the relationship:

$$P = K(T_{surface} - \text{TAT}) V \rho$$

where:
K is the heat transfer coefficient of the surface to the air
$T_{surface}$ is a surface temperature at a region
TAT is the total air temperature of the environment surrounding the structure
V is the free-stream air speed
$\rho$ is the density of the air surrounding the structure.

46. A controller according to claim 45, wherein the density of the air surrounding the structure is determined by the relationship:

$$\rho = \rho_0 T_0 \frac{e^{(-altitude/ref\_alt)}}{SAT}$$

Where:
$\rho_0$ is the air density at standard Temperature and Pressure
$T_0$ is the standard Temperature
altitude is the altitude of the structure (in ft)
ref_alt is a reference altitude (in ft)
SAT is the Static Air Temperature.

47. A controller according to claim 45, wherein the density of the air surrounding the structure is determined by the relationship:

$$\rho = \rho_0 \frac{P T_0}{P_0 SAT}$$

where:
$\rho_0$ is the air density at standard Temperature and Pressure
$T_0$ is standard Temperature
P is the Static Air Pressure
$P_0$ is the Standard Air Pressure
SAT is the Static Air Temperature.

48. Apparatus for controlling de-icing of a surface of a structure, the structure being exposable to an impinging airflow, the apparatus comprising:
a first heater thermally coupleable to a first region of structure exposable to an impinging airflow,
a first temperature sensor thermally coupled to the first heater for sensing the temperature of the first heater and for outputting a first temperature signal;
one or more second heaters thermally coupleable to a respective region of the structure,
for each of the one or more second heaters, a respective temperature sensor thermally coupled thereto for sensing the temperature of the respective second heater and for outputting a respective temperature signal;
a controller coupled to the first heater, first temperature sensor, each of the one or more second heaters and each of the respective temperature sensors and for controllably applying power to the first heater and one or more second heaters, the controller being configured to:
supply the first heater with a first power, the first power being sufficient to heat a surface of the structure at the first region;
supply each of the one or more second heaters with a respective power, the respective power being sufficient to heat a surface of the structure at the respective region;

control the power applied to each of the one or more second heaters such that the respective surface temperature is substantially the same as the surface temperature of the first region; and detect the presence of water or ice on the surface of a structure at a respective region by comparing a power consumed by the respective heater to achieve a temperature at the surface of the surface at the respective region with the a reference power for the respective heater, and controlling one or more of the first and second heaters in response to the detection of ice or water on the surface of the structure to de-ice the surface of the structure, wherein the reference power is a power for applying to the respective heater to achieve the same temperature at the surface of the structure at the respective region if the respective region of the structure was subjected to an environmental condition that was substantially devoid of water, and wherein the controller detects the presence of water or ice when the power consumed by the respective heater is greater than the reference power.

* * * * *